United States Patent
Dannenmaier et al.

(10) Patent No.: US 8,403,150 B2
(45) Date of Patent: Mar. 26, 2013

(54) END-CAP ASSEMBLY WITH PUMP HOSE FOR A FILTER AND FILTER COMPRISING SUCH AN END-CAP ASSEMBLY

(75) Inventors: Jürgen Dannenmaier, Balingen (DE); Björn Frederik Seidler, Scheebel (DE); Lennart Jönsson, Furulund (SE); Eddie Nilsson, Höör (SE); Francesco Ribolzi, Varese (IT)

(73) Assignee: Gambro Lundia AB (SE)

(*) Notice: Subject to any disclaimer, the term of this patent is extended or adjusted under 35 U.S.C. 154(b) by 1117 days.

(21) Appl. No.: 11/379,725

(22) Filed: Apr. 21, 2006

(65) Prior Publication Data

US 2009/0020468 A1 Jan. 22, 2009

Related U.S. Application Data

(63) Continuation of application No. PCT/EP2004/011707, filed on Oct. 18, 2004.

(30) Foreign Application Priority Data

Nov. 7, 2003 (EP) .................................... 03025640

(51) Int. Cl.
*B01D 19/00* (2006.01)
*B01D 27/08* (2006.01)
*B01D 35/30* (2006.01)
*B01D 27/00* (2006.01)

(52) U.S. Cl. .................. 210/435; 210/321.71; 210/188; 210/348; 210/416.1

(58) Field of Classification Search .................. None
See application file for complete search history.

(56) References Cited

U.S. PATENT DOCUMENTS

| | | | |
|---|---|---|---|
| 4,227,420 A | 10/1980 | Lamadrid |
| 4,231,871 A | 11/1980 | Lipps et al. |
| 4,263,808 A | 4/1981 | Bellotti et al. |
| 4,287,059 A | 9/1981 | Kume et al. |
| 4,293,413 A | 10/1981 | Schnell |
| 4,344,777 A | 8/1982 | Siposs |
| 4,345,999 A | 8/1982 | Sigdell et al. |
| 4,368,118 A | 1/1983 | Siposs |

(Continued)

FOREIGN PATENT DOCUMENTS

| | | |
|---|---|---|
| DE | 4027531 C1 | 7/1991 |
| EP | 0245782 A2 | 11/1987 |

(Continued)

OTHER PUBLICATIONS

WIPO, International Search Report, for PCT No. PCT/EP2004/012277, Published May 19, 2005, 3pgs.

(Continued)

*Primary Examiner* — Benjamin Kurtz
(74) *Attorney, Agent, or Firm* — Finnegan, Henderson, Farabow, Garrett & Dunner LLP

(57) ABSTRACT

An end-cap assembly for closing one end of a housing of a filter comprises an end-cap having an end wall; an inlet port extending through the end wall for connection to a first end of a pump hose of a peristaltic pump; and a first holder for securing a second end of the pump hose. The inlet port and the first holder are arranged relative to each other so that the pump hose forms a loop when the first end of the pump hose is connected to the inlet port and the second end of the pump hose is secured by the holder.

25 Claims, 8 Drawing Sheets

U.S. PATENT DOCUMENTS

| | | | |
|---|---|---|---|
| 4,379,452 A | 4/1983 | DeVries | |
| 4,412,916 A | 11/1983 | Kell | |
| 4,433,971 A | 2/1984 | Lindsay et al. | |
| 4,436,620 A | 3/1984 | Bellotti et al. | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,493,693 A | 1/1985 | Bilstad et al. | |
| 4,582,598 A | 4/1986 | Bilstad et al. | |
| 4,605,503 A | 8/1986 | Bilstad et al. | |
| 4,617,115 A | 10/1986 | Vantard | |
| 4,623,450 A | 11/1986 | Vantard et al. | |
| 4,666,598 A | 5/1987 | Heath et al. | |
| 4,676,467 A | 6/1987 | Palsulich | |
| 4,765,888 A | 8/1988 | Barthe et al. | |
| 4,798,090 A | 1/1989 | Heath et al. | |
| 4,806,135 A | 2/1989 | Siposs | |
| 4,824,339 A | 4/1989 | Bainbridge et al. | |
| 5,130,020 A * | 7/1992 | Meckstroth | 210/264 |
| 5,200,090 A | 4/1993 | Ford et al. | |
| 5,441,636 A | 8/1995 | Chevallet et al. | |
| 5,468,388 A | 11/1995 | Goddard et al. | |
| 5,707,431 A | 1/1998 | Verkaart et al. | |
| 5,744,047 A | 4/1998 | Gsell et al. | |
| 5,849,065 A | 12/1998 | Wojke | |
| 6,176,903 B1 | 1/2001 | Wamsiedler | |
| 6,206,954 B1 | 3/2001 | Schnell et al. | |
| 6,361,518 B1 | 3/2002 | Brierton et al. | |
| 6,582,386 B2 | 6/2003 | Min et al. | |
| D479,320 S | 9/2003 | O'Mahony et al. | |
| 2003/0138349 A1 | 7/2003 | Robinson et al. | |
| 2007/0181488 A1* | 8/2007 | Dannenmaier et al. | 210/450 |

FOREIGN PATENT DOCUMENTS

| | | |
|---|---|---|
| EP | 0292445 A1 | 11/1988 |
| EP | 0591896 A2 | 4/1994 |
| FR | 2513884 | 4/1983 |
| WO | WO-00125843 A1 | 5/2000 |

OTHER PUBLICATIONS

WIPO, International Search Report, for PCT No. PCT/EP2004/012528 Published May 19, 2005, 4pgs.

WIPO, International Search Report, for PCT No. PCT/EP2004/011707 Published May 19, 2005, 2pgs.

WIPO, International Search Report, for PCT No. PCT/EP2004/012372 Published Jun. 16, 2005, 3pgs.

EPO, European Search Report, Application No. 1529545, Published Jun. 1, 2005, 3pgs.

EPO, European Search Report, Application No. 1530995, Published May 18, 2005, 2pgs.

EPO, European Search Report, Application No. 1532994, Published May 25, 2005, 3pgs.

* cited by examiner

END-CAP ASSEMBLY WITH PUMP HOSE FOR A FILTER AND FILTER COMPRISING SUCH AN END-CAP ASSEMBLY

This application is a continuation of PCT/EP2004/011707, filed Oct. 18, 2004, which claims foreign priority to European Patent Office (EPO) 03025640.8.

The present invention relates to an end-cap assembly for a filter, in particular, to an end-cap assembly for a hollow fiber filter. The invention also relates to a filter comprising such an end-cap assembly.

A conventional hollow fiber filter comprises a tubular housing, a semi-permeable membrane in the form a bundle of hollow fibers extending within the housing and secured thereto at both ends, and two end-caps closing the housing at both ends. The ends of the fibers are secured to the housing by a potting material in which they are embedded. The potting material forms a disk that extends perpendicularly to the longitudinal axis of the housing. The ends of the fibers open on an outer surface of the disks of potting material. By construction, such a hollow fiber filter therefore comprises a first and the second compartments isolated from each other: the first compartment includes the interior of the hollow fibers and the space delimited at each end of the filter between the outer surface of the disk of potting material and the inner surface of the end-cap, and the second compartment includes the space outside of the hollow fibers that is delimited by the inner surface of the housing and the inner surface of the disks of potting material. Each end-cap comprises an inlet/outlet nozzle through which a liquid can be flown into and out of the first compartment. The housing is also fitted with one or two nozzle that gives access to the second compartment.

Hollow fiber filters are used in particular in various extracorporeal treatments of blood, such as hemodialysis, hemofiltration, hemodiafiltration, plasmapheresis. The same type of filter, usually referred to as hemodialyzer or hemofilter, is used for hemodialysis, hemofiltration, hemodiafiltration. The main difference between a hemodialyzer and a plasmafilter (i.e. a filter used in plasmapheresis) is the pore size of their respective membrane, a membrane for plasmapheresis allowing the proteins contained in blood to migrate therethough, whereas a membrane for hemodialysis does not.

In all these treatments, blood is withdrawn from the patient, flown through the first compartment of a hollow fiber filter, and returned to the patient. In hemodialysis, a dialysis liquid is simultaneously flown though the second compartment of the filter and the metabolic wastes (urea, creatinine) contained in blood migrate by diffusion through the membrane into the second compartment. In hemofiltration, a pressure difference is created across the membrane so that plasma water flows through the membrane into the second compartment of the filter. Here, metabolic wastes migrate by convection into the second compartment. In order to compensate for the loss of bodily fluid, the patient is simultaneously injected a sterile substitution solution. Hemodiafiltration is a combination of hemodialysis and hemofiltration, and, in this treatment, a dialysis liquid is flown through the second compartment and a substitution liquid is injected into the patient. In plasmapheresis, a pressure difference is created across the membrane so that plasma (i.e. plasma water and proteins) flows through the membrane into the second compartment of the filter. Once treated, the plasma is returned to the patient.

A machine for performing any of the above treatments comprises a peristaltic pump for withdrawing blood from the patient through a so-called "arterial line" connected at one end to the vascular circuit of the patient and at the other end to the inlet nozzle of the first compartment of a filter, for pumping blood into the filter, and for returning blood to the patient through a so-called "venous line" connected at one end to the outlet nozzle of the first compartment of the filter and at the other end to the vascular circuit of the patient. The machine also usually comprises a first blood pressure sensor for measuring the pressure of blood in the arterial line upstream of the pump, a second blood pressure sensor for measuring the pressure of blood in the arterial line downstream of the pump, a third pressure sensor for measuring the pressure of blood in the venous line, a bubble detector for detecting air bubbles in the venous line and a clamp for closing the venous line, for example when air bubbles are detected by the bubble detector.

An arterial line typically comprises the following components connected together by segments of flexible tubes: a first Luer connector for connection to an arterial cannula, an arterial bubble trap, a pump hose for cooperating with the rotor of the peristaltic pump of the machine, and a second Luer connector for connection to the inlet nozzle of the first compartment of a filter. A venous line typically comprises the following components connected together by segments of flexible tubes: a first Luer connector for connection to the outlet nozzle of the first compartment of a filter, a venous bubble trap, and a second Luer connector for connection to a venous cannula. Usually, the first and third pressure sensors of the machine are connected to the arterial and venous bubble trap respectively, when the machine, the arterial line the venous line and the filter are assembled in view of a treatment.

A dialysis machine further comprises a dialysis liquid generator that can be connected through a supply line to the inlet nozzle of the second compartment of a hemodialyzer. The dialysis machine also comprises a waste line by which the outlet nozzle of the hemodialyzer can be connected to the drain. A hollow fiber ultrafilter of similar construction as described above can be connected to the supply line so that an extra pure dialysis liquid is supplied to the hemodialyzer. The invention also applies to such an ultrafilter.

The assemblage of the arterial and venous line to the filter and to the machine in preparation for a treatment is time consuming, and an object of the invention is to design and end-cap assembly that facilitates such an assemblage.

According to the invention, an end-cap assembly for closing one end of a housing of a filter, comprises:
an end-cap having an end wall;
an inlet port extending through the end wall for connection to a first end of a pump hose of a peristaltic pump; and
a first holder for securing a second end of the pump hose, wherein the inlet port and the first holder are arranged relative to each other so that the pump hose forms a loop when the first end the pump hose is connected to the inlet port and the second end of the pump hose is secured by the holder.

Within the frame of the invention, "inlet port" means the passage through the end wall of the end-cap as well as any straight or bent nozzle or channel that may extend this passage on the outer side of the end cap.

This arrangement facilitates the loading of a filter in a machine having a peristaltic pump for circulating a liquid in the filter.

According to one variant of the invention, the inlet port and the first holder are arranged relative to each other so that the loop formed by the pump hose substantially extends in a plane that is inclined with respect to a plane perpendicular to a central axis of the end-cap. In particular, the inlet port and the first holder are arranged relative to each other so that the first end and second end of the pump hose are longitudinally spaced apart from each other with respect to the central axis of the end-cap and the second end of the pump hose is further apart from the end-cap than the first end of the pump hose.

When a hemodialyzer or a hemofilter comprising this end-cap assembly is hold in the usual operative position, i.e. substantially vertical, with the end-cap assembly being at the lowest point, this arrangement helps degas the pump hose, in particular when a circuit including the filter is primed with a liquid (e.g. a sterile saline liquid) before the filter is used for treating blood.

According to another variant of the invention, the inlet port and the first holder are arranged relative to each other so that the loop formed by the pump hose substantially extends in a plane parallel to a central axis of the end-cap when the first end of the pump hose is connected to the inlet port and the second end of the pump hose is secured by the first holder.

According to one feature of the invention, in order to facilitate the packaging of a filter comprising the end-cap assembly, the first holder is removably mounted on the end-cap.

According to another feature of the invention, the end-cap assembly comprises a second holder for holding the pump hose between the inlet port and the first holder.

According to yet another feature of the invention, the end-cap assembly comprises a pump hose connected to the inlet port and the holder, e.g. by gluing or welding.

Other additional or alternative features of the invention are as follows:

- The inlet port is offset with respect to a central axis of the end-cap.
- The inlet port comprises a first portion furthest to the end wall, a second portion closest to the end wall, and an intermediate portion connecting the first portion to the second portion, wherein the first portion has an axis slightly inclined with respect to a plane perpendicular to a central axis of the end-cap, the second portion flares towards an interior of the end-cap along an axis generally parallel to the central axis of the end-cap and the intermediate portion has a curvature adapted to facilitate a smooth an unimpeded flow of a liquid pumped into the end cap.
- The first holder comprises a tubular connector for connecting the pump hose to a tube.
- The first holder comprises a clip for snugly engaging a tubular connector for connecting the pump hose to a tube. The tubular connector is removable and the clip is designed to resiliently engage and lock the tubular connector.
- The end-cap assembly comprises at least one infusion port connected to the inlet port and a pressure measurement port connected to the inlet port for measuring a pressure of liquid downstream of the pump hose.
- The end-cap assembly comprises at least one infusion port connected to the first holder and a pressure measurement port connected to the first holder for measuring a pressure of liquid upstream of the pump hose.

Another object of the invention is pump hose for a peristaltic pump adapted to the end cap assembly of the invention. Such a pump hose has a first end fitted with a connecting element for connection to the inlet port and a second end fitted with a connecting element for connection to the first holder Still another object of the invention is a filter comprising such an end-cap assembly.

Other features and advantages of the invention will appear on reading the detailed description that follows. Reference will be made to the appended drawings in which.

Figure 1:
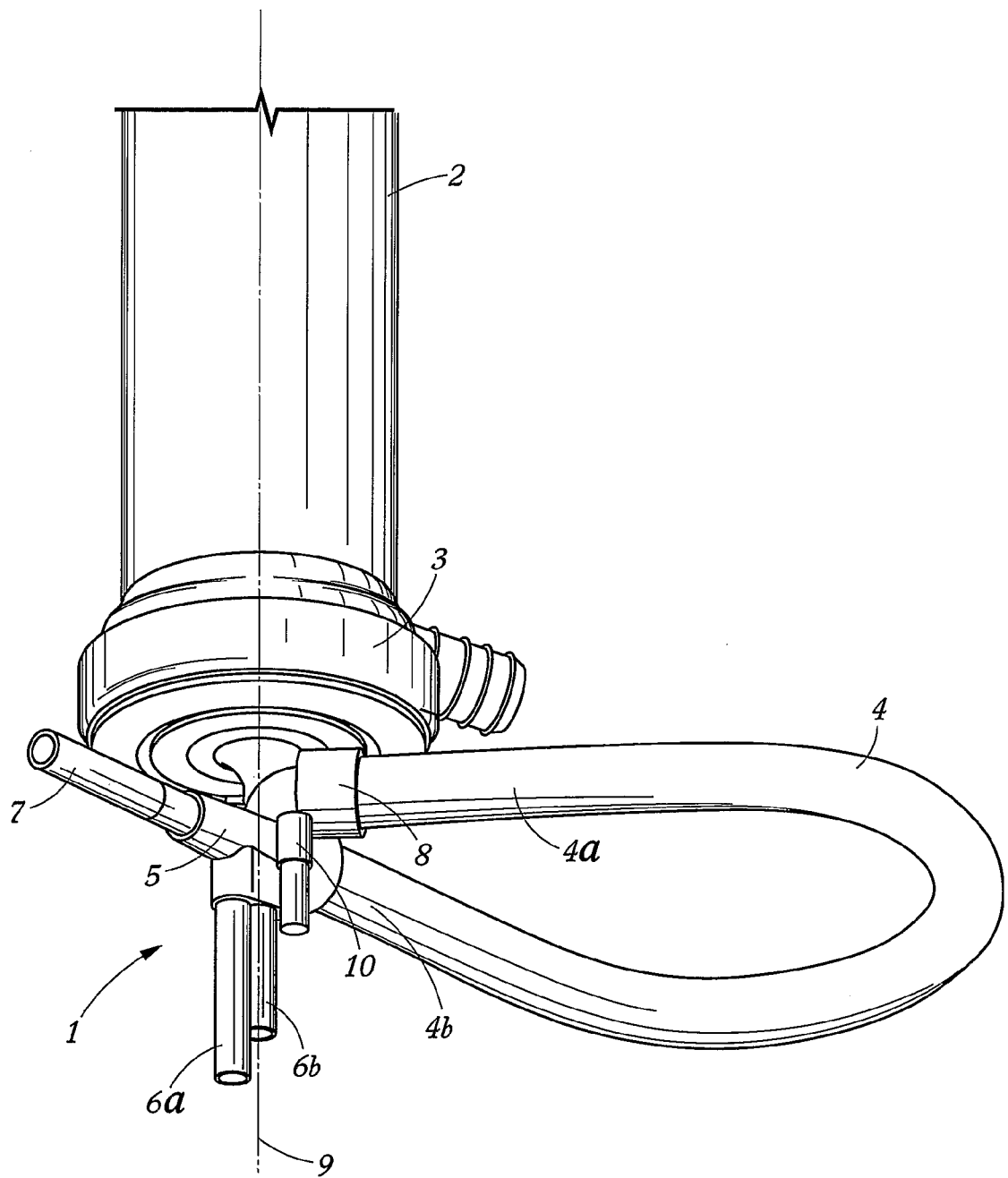
FIG. 1 is a perspective view of a portion of a hollow fiber filter comprising an end-cap assembly according to the invention.

FIG. 1 shows an end-cap assembly 1 mounted at one end of a tubular housing 2 of a filter. The end-cap assembly 1 comprises an end-cap 3 having a slightly cambered circular end wall connected to a cylindrical peripheral wall by which the end-cap 3 is secured to the housing 2 of the filter. When the end-cap 3 is mounted on the housing 2 of a filter, as shown, the circular end wall of the end-cap 3 is substantially perpendicular to the longitudinal axis of the housing 2, and the central axis 9 of the end-cap 3 coincides with the longitudinal axis of the housing 2. The end-cap assembly 1 further comprises a nozzle 8 made integral with the end-cap 3 so as to form an inlet port that gives access to the interior of the end-cap 3, and a tubular holder 5 for an end of a pump hose 4 of a peristaltic pump. The tubular holder 5 is secured to the nozzle 8 by welding or gluing or it can be formed integral with the nozzle 8. The tubular holder 5 has a larger section at one end for connection to a pump hose 4 and a smaller section at the other end for connection to a tube 7 forming the downstream part of the arterial blood line of an extracorporeal blood treatment system.

The tubular holder 5 is so positioned with respect to the nozzle 8 as to be further apart from the end-cap 3 than the nozzle 8. It results from this arrangement that, when a first (or downstream) end 4a of a pump hose 4 is connected to the inlet port 8 and the second (or upstream) end 4b of the pump hose 4 is connected to the tubular holder 5, the first end 4a of the pump hose 4 is offset from the second end 4b along the central axis 9 of the end-cap 3. When the end-cap assembly 1 is in an operative position, i.e. at a lower point of a filter held vertical, the tubular holder 5 and the upstream end 4b of a pump hose 4 are therefore lower than the nozzle 8 and the downstream end 4a of the pump hose 4.

Also, the inlet port 8 and the tubular holder 5 are so positioned with respect to each other that when a first end 4a of a pump hose 4 is connected to the inlet port 8 and the second end 4b of the pump hose 4 is connected to the tubular holder 5, the pump hose 4 forms a loop that extends in a plan that is slightly inclined with respect to a plan perpendicular to the central axis 9 of the end-cap assembly 1. Since the tubular holder 5 is lower that the nozzle 8 when the end cap assembly 1 is in an operational position, this arrangement helps gas bubbles move though the hose into the filter and prevents the stagnation of gas bubbles in the pump hose 4. A desired angle of inclination of the looped hose 4 with respect to a plane perpendicular to the central axis 9 of the end-cap assembly 1 may be comprised between 3 to 7 degrees, and preferably be about 5 degrees.

The looped pump hose 4 is adapted to readily cooperate with a peristaltic pump of the rotary type upon connection of the filter to a treatment device (e.g. a dialysis machine). A rotary peristaltic pump comprises a rotor generally bearing two rollers at its periphery. The rotor is mounted in a support having a semi-circular wall that partially surrounds the rotor and defines a semi-annular gap in which the pump hose 4 can be received. When the rotor rotates, the rollers alternately engage the pump hose 4 and squeeze it against the semicircular wall while moving along a circular path, thereby pushing the liquid contained in the pump hose 4 towards the downstream end 4a of the hose.

The end-cap assembly 1 further comprises two Infusion/injection ports 6a, 6b connected to the tubular holder 5, which can be used for the injection of various substances (e.g. heparin or a substitution solution) to the liquid (e.g. blood) flowing through the filter. One of these ports can also be used as a pressure measurement port for connection to a pressure sensor for measuring the pressure of the liquid upstream of the pump hose 4. The end-cap assembly 1 also comprises a pressure measurement port 10 connected to the inlet port 8 for connection to a pressure sensor for measuring the pressure of the liquid entering the first compartment of the filter.

Figure 2:
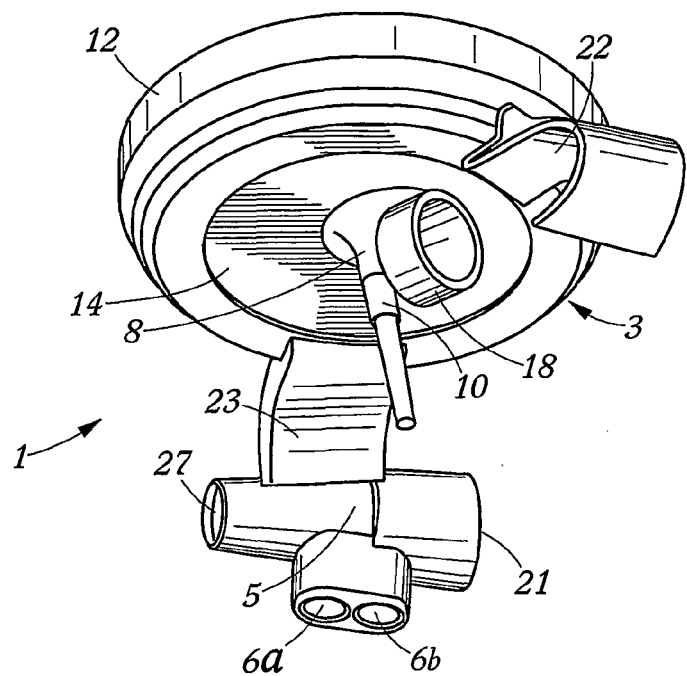
FIG. 2 is a perspective view of a second embodiment of an end-cap assembly according to the invention.
Figure 3:
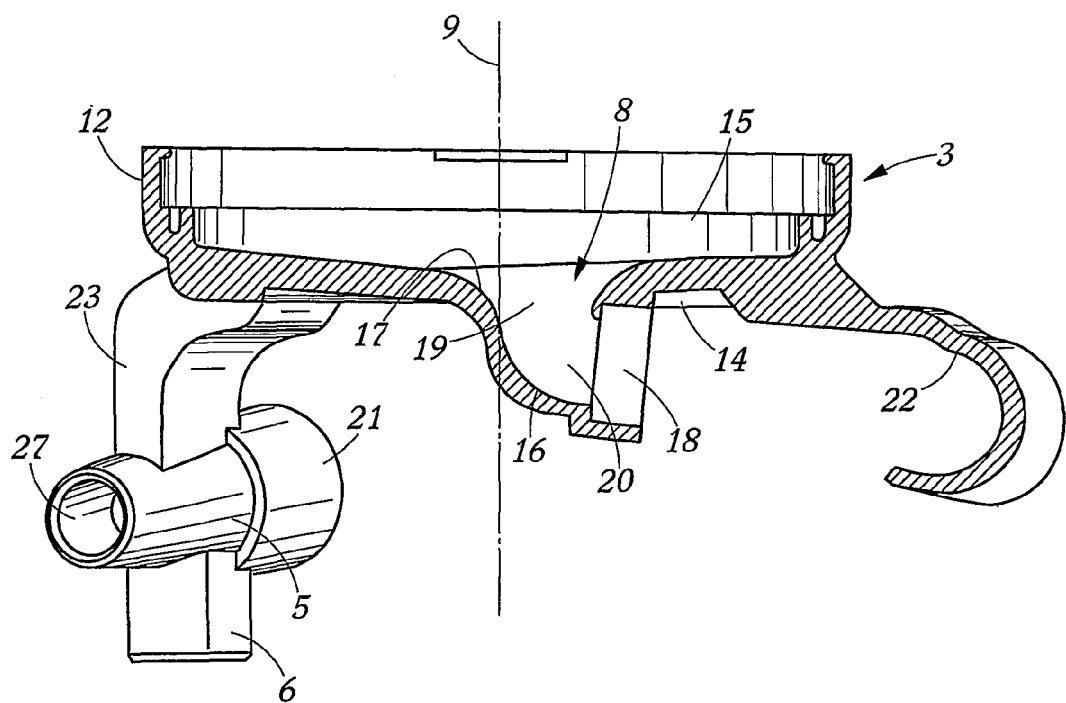
FIG. 3 is a cross-section view of the end-cap assembly of FIG. 2.
Figure 4:
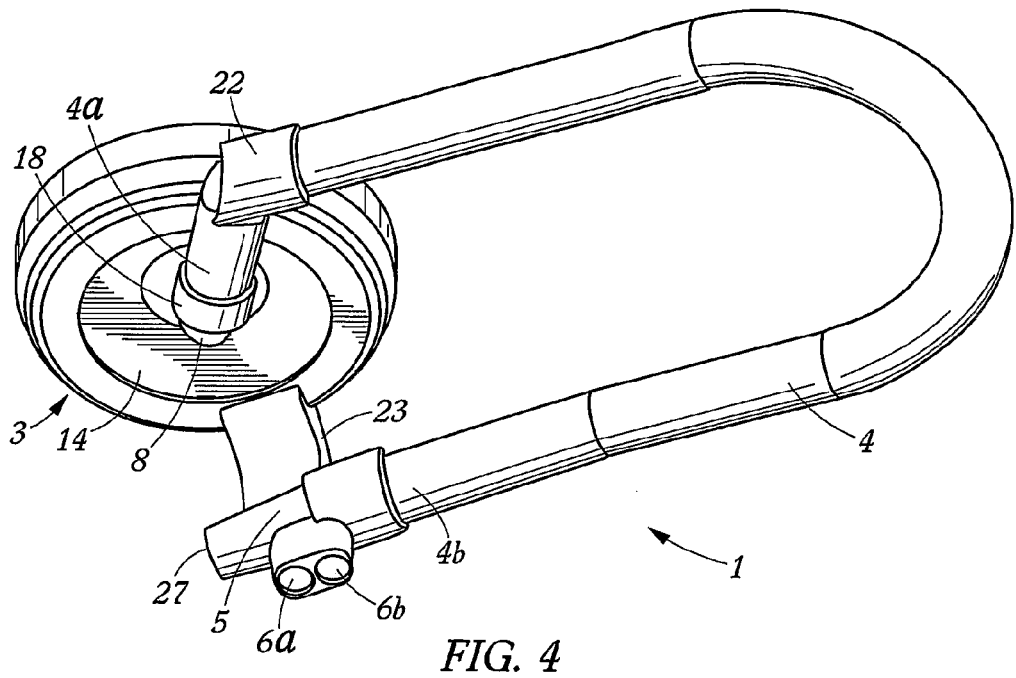
FIG. 4 is a perspective view of the end-cap assembly shown in FIGS. 2 and 3 fitted with a pump hose.

FIGS. 2 to 4 show a second embodiment of the end-cap assembly 1 of the invention. In FIGS. 2 and 3, the end-cap assembly 1 is represented without a pump hose connected thereto, whereas in FIGS. 4 and 5 a pump hose 4 is connected to the inlet port 8 and to the holder 5, 23. The end-cap 3 comprises a circular end-wall portion 14 connected to a peripheral wall portion 12 that is designed for securing the end-cap 3 to the housing of a filter. The end-cap 3 has a central axis 9 that coincides with the longitudinal axis of the tubular housing of a filter when the end-cap is mounted at one end of such a housing. The circular end wall portion 14 and the peripheral wall portion 12 define an interior region 15 of the end-cap 3. The interior region 15 forms a header-chamber when the end-cap 3 is mounted at one end of the housing of a filter.

Figure 5:
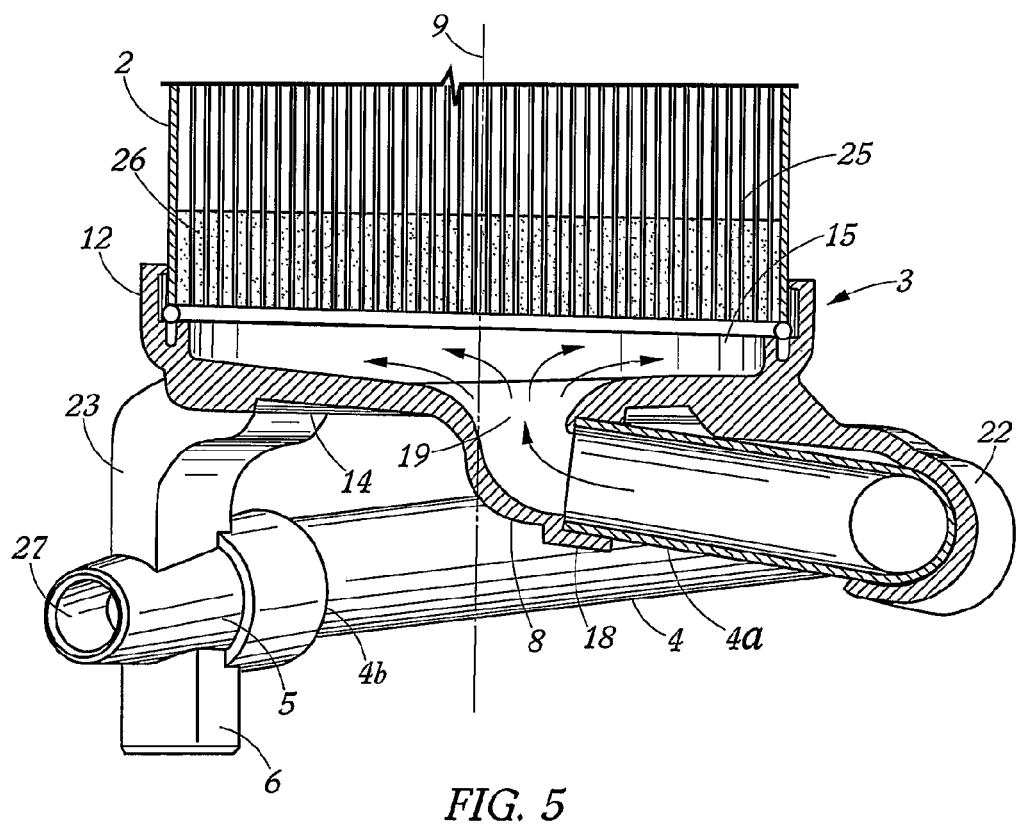
FIG. 5 is cross-section view of the end-cap assembly of FIGS. 2 to 4 mounted on an end of a hollow fiber filter.

The end-cap assembly 1 shown on FIGS. 2 to 5 has an inlet port 8 that is eccentric with respect to the central axis 9 of the end-cap 3 and is formed integral with the end-wall 14 and of the end-cap 3. The inlet port 8 comprises a first (upstream) portion 18 furthest to the end wall 14, a second (downstream) portion 19 closest to the end wall 14, and an intermediate portion 20 connecting the first portion 18 to the second portion 19. The first (upstream) portion 18 is cylindrical and has a longitudinal axis slightly inclined with respect to a plane perpendicular to the central axis 9 of the end-cap 3. The second (downstream) portion 19 flares towards the interior 15 of the end-cap 3 along an axis generally parallel to the central axis 9. The intermediate portion 20 has a curvature 16 selected so as to facilitate a smooth an unimpeded flow of a liquid pumped into the end cap 3. At its connection to the end wall 14, the downstream flaring portion 19 also has a curvature 17 selected so as to evenly direct a liquid pumped into the end cap 3 towards the apertures of the hollow fibers 25 at the outer surface of a disk 26 of potting material, when the end-cap assembly is mounted at one end of a filter housing 2 (FIG. 5). The geometry of the inlet port 8 therefore ensures a smooth passage and distribution of a liquid therethrough and into the interior region 15. The radius of the curvature 16 of the intermediate portion 20 and the radius of the curvature 17 of the second portion 19 may be equal. A suitable value for both radii lies in the range of about 6 to 12 mm, preferably about 9 mm.

The end-cap assembly 1 further comprises a first holder for a pump hose 4 having a leg 23 protruding at the periphery of the end-cap 3 and a tubular connector 5 connected to the leg 23 so that the longitudinal axis of the tubular connector 5 is substantially parallel to a line tangential to the circular end wall portion 14 of the end-cap 3. It results from this arrangement that the inlet port 8 and the tubular connector 5 are spaced apart with respect to the central axis 9, both axially and longitudinally, the inlet port 8 being closer to the end-cap 3 than the connector 5. A pump hose 4 connected to the tubular connector 5 and the inlet port 8 forms a loop that is therefore slightly inclined with respect to a plan perpendicular to the central axis 9, with the upstream end 4b of the pump hose 4 lower than the downstream end 4a of the pump hose 4 when the end cap assembly 1 is in an operational position as shown in FIG. 5. A suitable angle of inclination for helping degas the pump hose 4 during the priming of a filter is in the range of 3 to 7 degrees, preferably 5 degrees.

The first holder 5, 23 may be formed integral with the end-cap 3, or it may be fixed to the end-cap 3 for example by bonding or by welding. The tubular connector 5 comprises a first socket 21 of larger section at one end for connection to a pump hose 4 and a second socket 27 of a smaller section at the other end for connection to a tube (e.g. an arterial blood line). The socket 27 can comprise a Luer connection element (not shown) for attachment to a tube fitted with a complementary Luer connection element. The connector 5 also comprises two ports 6a, 6b that can be used for infusing a liquid into the filter or to measure the pressure in the liquid upstream of a peristaltic pump.

The end-cap assembly represented in FIGS. 2 to 5 further comprises a second holder 22 for the pump hose 4 comprising an arm extending outwards, from the periphery of the end-cap 3, substantially opposite the first holder 5, 23 with respect to the inlet port 8. The second holder 22 comprises a grip at its outer end for receiving and holding a portion of the pump hose 4. The inlet port 8 and the second holder 22 are so arranged with respect to each other that, when the first end 4a of a pump hose 4 is secured to the inlet port 8 and the second end 4b of the pump hose 4 is secured to the first holder 5, 23, the pump hose 4 has a first portion that extends straight from the inlet port 8 to the second holder 22 and a second U-shaped portion that extends from the second holder 22 to the first holder 5, 23. In this arrangement, the pump hose 4 is bent by the second holder 22, just upstream of the second holder 22 (FIG. 4). The second holder 22 gives rigidity to the pump hose 4 and thereby facilitates the positioning of the pump hose 4 around the rotor of a peristaltic pump of a treatment machine. The second holder 22 can be formed integral with the end-cap 3, or it can be attached to the end-cap by e.g. bonding or welding.

FIG. 5 shows the end-cap assembly 1 of FIGS. 2 to 4 connected to the housing 2 of a hollow fiber filter. A liquid, represented by arrows, flows through the pump hose 4 and enters via the inlet port 8 into the header chamber 15 of the filter, which is delimited by the interior surface of the end-cap 3 and the outer surface of a disk of potting material 26 in which one end of a bundle of hollow fibers 25 is embedded.

Figure 6:
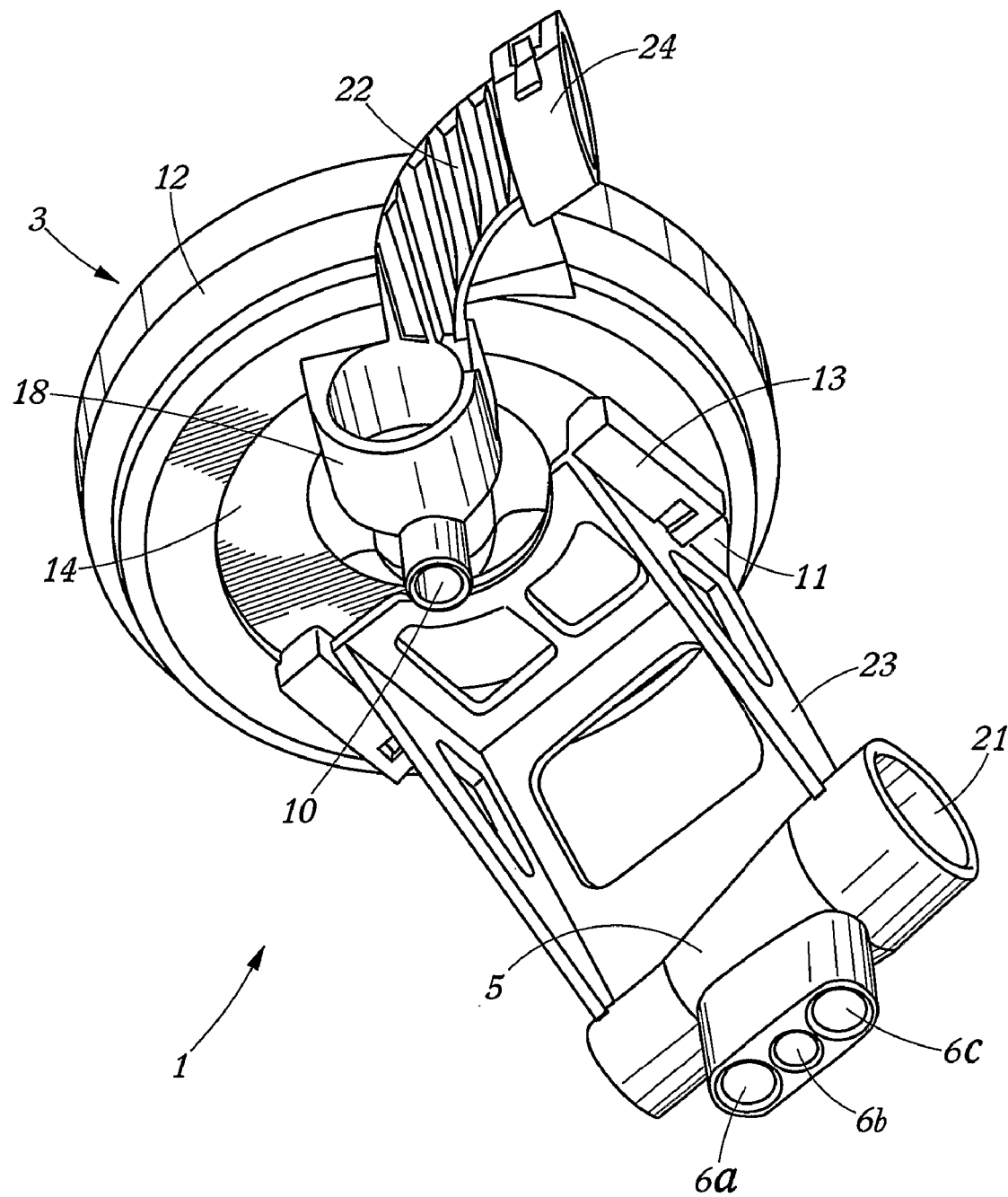
FIG. 6 is a perspective view of a third embodiment of an end-cap assembly according to the invention.

FIG. 6 shows a third embodiment of the end-cap assembly according to the invention. The first holder 5, 23 of this end-cap assembly is removable. The end-cap 3 comprises a fixation element in the form of two parallel grooves 13, and the leg 23 of the holder comprises a complementary fixation element in the form of two parallel tongues 11 designed to snugly fit in the grooves 13 when they are engaged therein. The tubular connector 5 comprises three ports 6a, 6b, 6c opening opposite the end-cap 3, which can be used for injecting or infusing various liquids (e.g. heparin and a substitution solution) and for connection to a pressure sensor. In this embodiment, the second holder 22 is connected to the inlet port 8 and it comprises a curved portion that leads to a tubular clip 24 forming the outer end of the holder. The clip 24 is resilient and can be opened so as to receive a portion of a pump hose that it snugly holds when closed. The curved portion of the second holder 22 forms a partial cradle for a portion of pump hose when a pump hose is connected to the inlet port 8 ant to the tubular connector 5, while passing through the clip 24. Here also it can be noted that the respective dimension and orientation of the inlet port 6 and the connector 5 are such that they are spaced apart axially and longitudinally with respect to the central axis of the end-cap 3, and that a pump hose connected thereto would form a loop slightly inclined with respect to a plane perpendicular to this central axis.

Figure 7:
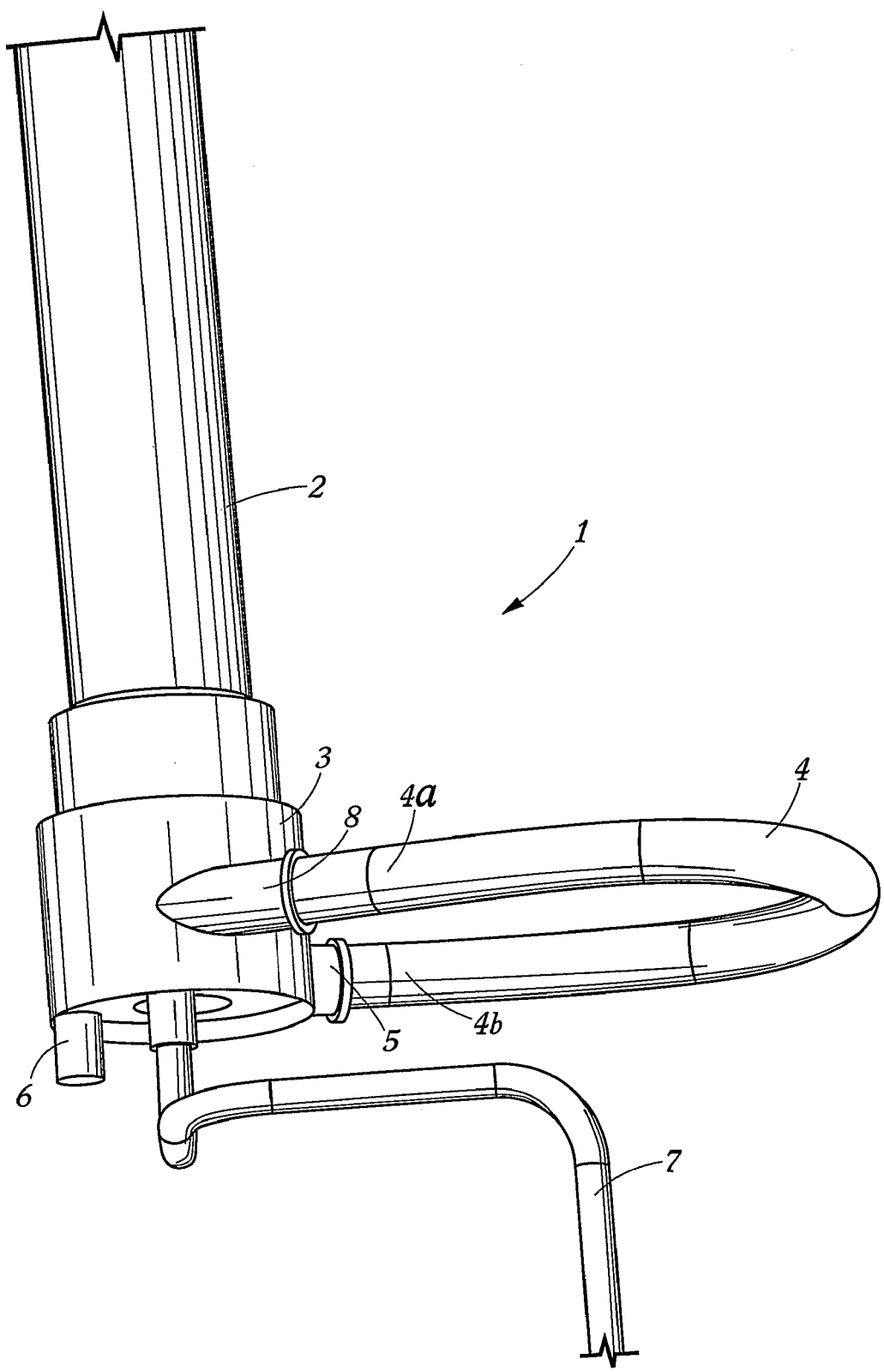
FIG. 7 is a perspective view of a fourth embodiment of an end-cap assembly according to the invention.
Figure 8:
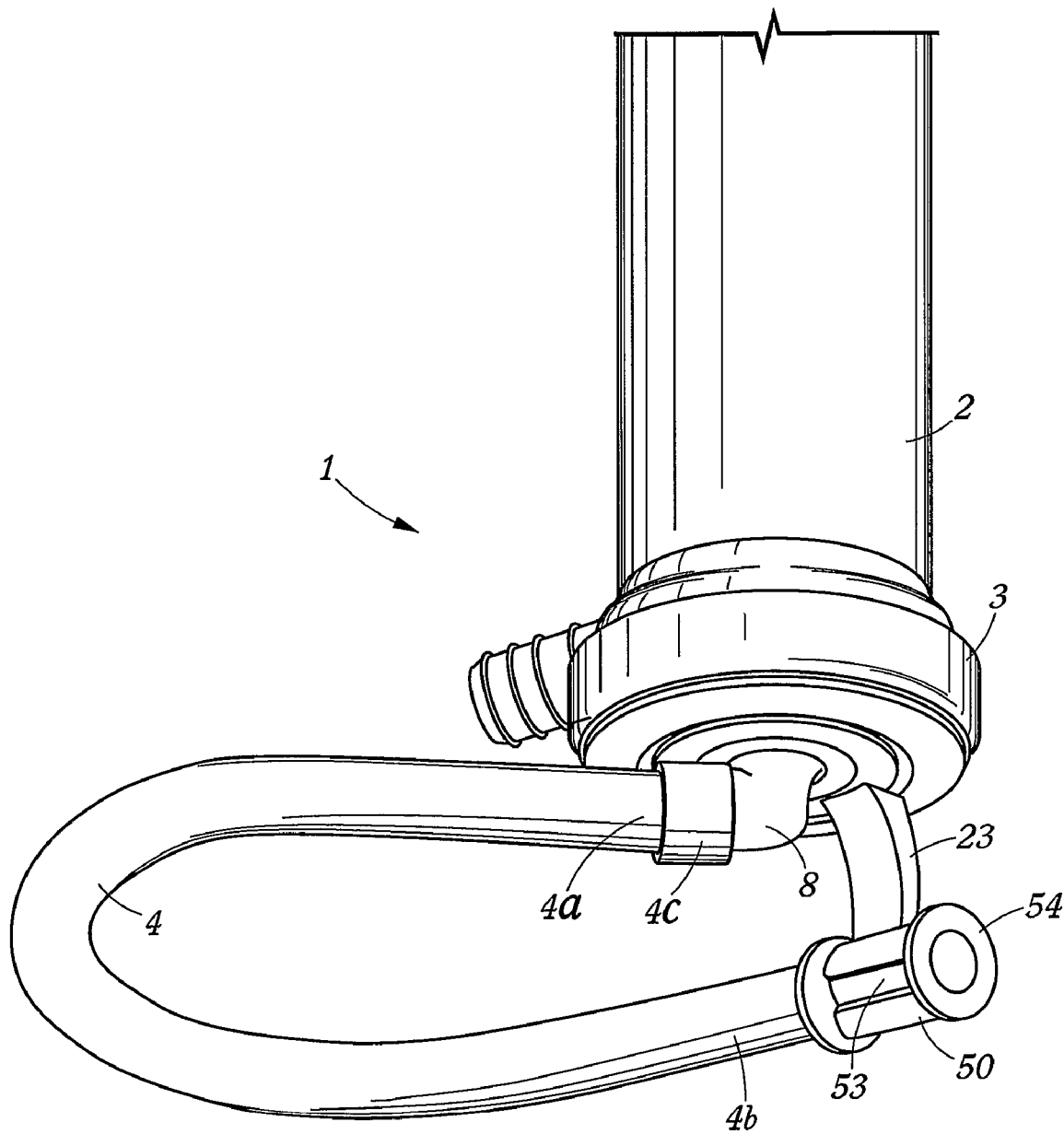
FIG. 8 is a perspective view of a fifth embodiment of an end-cap assembly according to the invention.
Figure 9A:
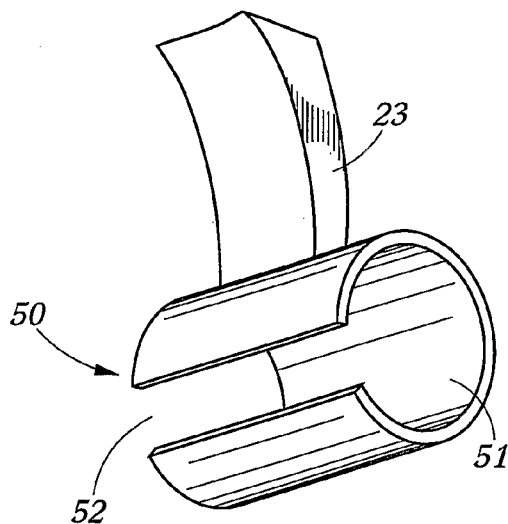
FIGS. 9a and 9b are perspective views of the two parts of the holder of the end-cap assembly of FIG. 8.
Figure 9B:
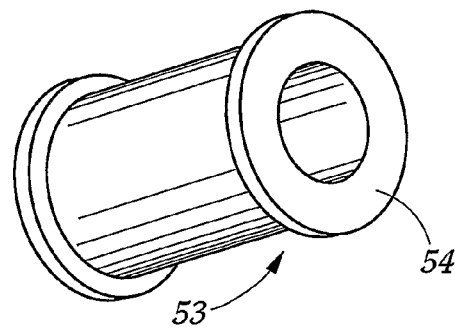

FIG. 7 shows a fourth embodiment of the end-cap assembly according to the invention. In this embodiment, the end-cap 3 comprises a tubular skirt to which an end portion of the inlet port 8 and of an end portion the holder 5 are connected so as to lie in a plane substantially perpendicular to the longitudinal axis of the filter. A pump hose 4 is connected to the inlet port 8 and to the connector 5 and forms a loop that extends in the same plane.

FIGS. 8 to 11b show a fifth embodiment of the end-cap assembly 1 according to the invention. In this embodiment, the holder does not comprise a tubular connector as in the embodiments of FIGS. 2 to 6, but instead its leg 23 is connected to and made integral with a resilient clip 50 having a C-shaped socket 51. The clip 50 has a longitudinal slit-like mouth 52 for allowing the engagement of a tubular connector 53 into the socket 51. The connector 53 has an outside diameter corresponding to the diameter of the C-shaped socket 51 and it comprises two circular end flanges 54 for preventing the connector 53 from longitudinally moving within the socket 51 when the connector 53 is engaged in the clip 50.

The tubular connector 53 is connected to the second end 4b of a pump hose 4, the first end 4a of which is either permanently connected to the inlet port 8 of the end-cap 3 or comprises a connecting element 4c, for example of the Luer type, for connection to a complementary connecting element included in the outlet port 8.

Figure 10A:
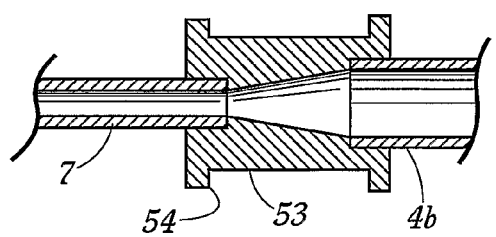
FIGS. 10a and 10b are longitudinal cross section views of two embodiments of the tubular connector of the holder of the end-cap assembly of FIG. 8.
Figure 11A:
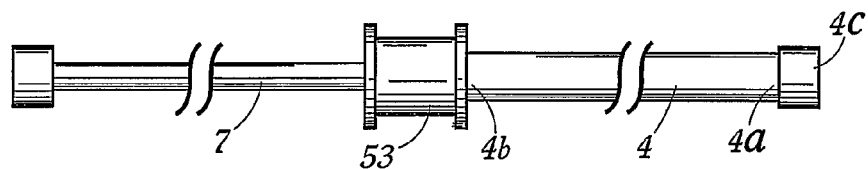
FIGS. 11a and 11b are plan views of two arterial blood lines designed to equip the end-cap assembly of FIG. 8.

The tubular connector 53 can also be pre-connected to a tube 7, as shown in FIGS. 10a and 11a, which represent an arterial blood line in which the tube 7 used for supplying blood from a patient to a hemodialyzer has a smaller diameter than the diameter of the pump hose 4. In such a case, the inner bore of the connector 53 comprises a first end portion with a smaller diameter corresponding to the outer diameter of the tube 7, a second end portion with a larger diameter corresponding to the outer diameter of the pump hose 4 and an intermediary portion flaring from the first end portion to the second end portion. The arterial blood line comprises a connecting element at both ends, one of which is the connector element 4c adapted to the inlet port 8, the other connector element being designed for connection to a cannula.

Figure 10B:
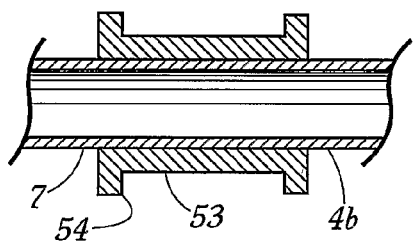
Figure 11B:
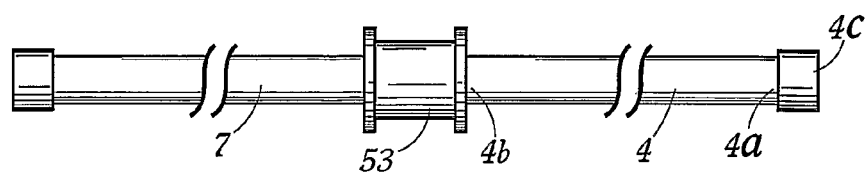

When an arterial blood line comprises a pump hose 4 and a supply tube 7 having the same diameter, the internal bore of the connector 53 is cylindrical and corresponds to the outer diameter of the pump hose 4 and the tube 7 that can be made of the same piece of tubing (see FIGS. 10b and 11b). In this case, the connector 53 is merely slipped on the piece of tubing before being glued thereto at the appropriate location.

Figure 12:
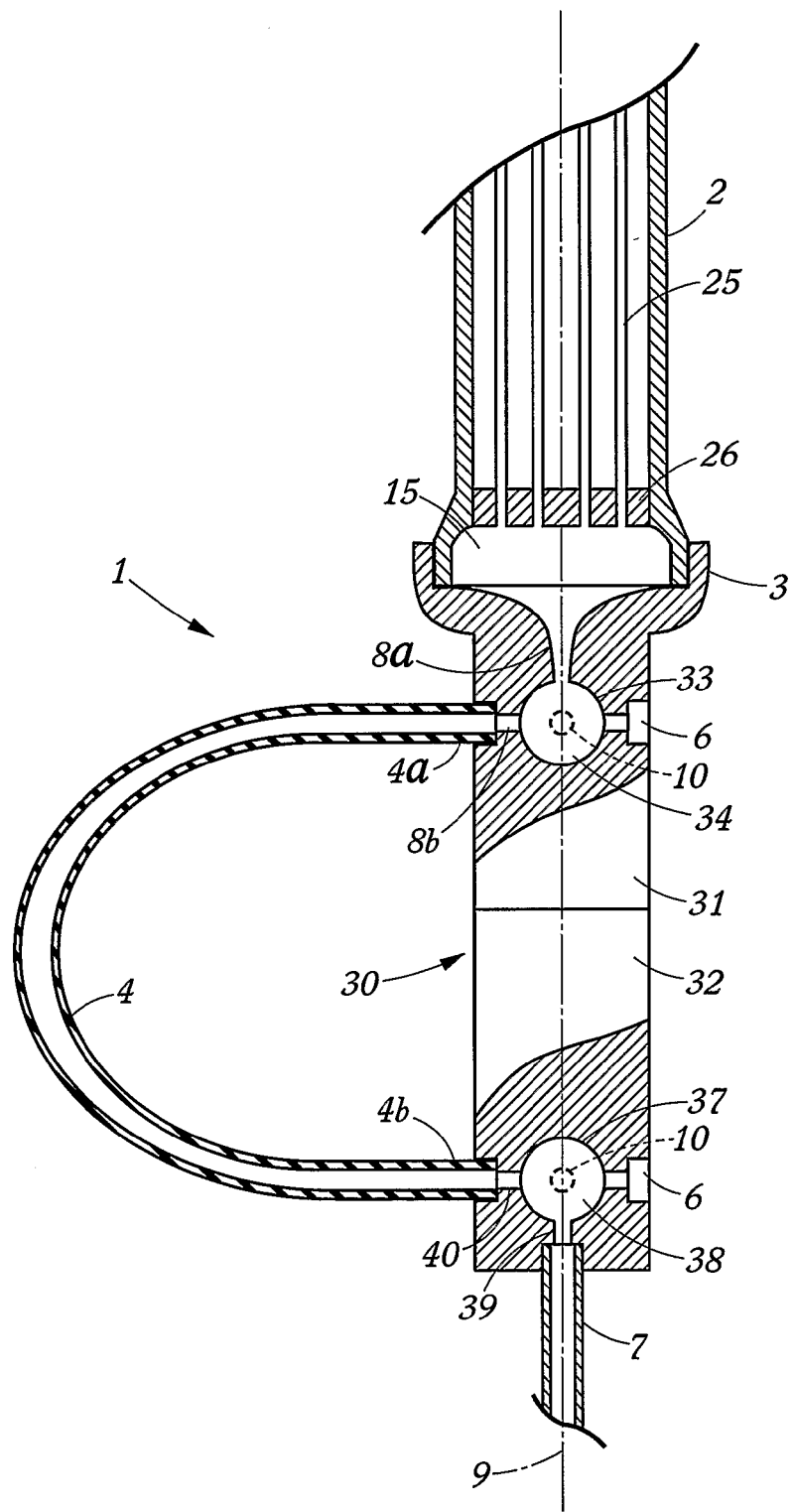
FIG. 12 is a longitudinal cross section view of a sixth embodiment of an end-cap assembly according to the invention.

FIG. 12 shows a sixth embodiment of the end-cap assembly 1 according to the invention. This end-cap assembly substantially differs from the previously described embodiments in that it is designed to hold a pump hose 4 in a plane containing the central axis b of the end-cap 3.

In more details, FIG. 12 represents an end portion of a filter having a tubular housing 2 containing a bundle of hollow fibers 25 secured to the housing 2 at the end thereof by a disk of potting material 26 in which the end of the fibers 25 are embedded. The housing 2 is closed by an end-cap 3 having a circular end wall whose central axis 9 coincides with the longitudinal axis 9 of the housing 2. A pump hose support 30 in the form of an elongated rectangular parallelepiped is connected to the end-cap 3 so that the longitudinal axis of the support 30 coincides with the central axis 9 of the end-cap 3. The pump hose support 30 comprises two separate parts 31 and 32 that can be connected together by a mechanical coupling (not shown).

The first part 31 of the pump hose support 30, which can be made integral with the end-cap 3, comprises a pressure measurement chamber 33 having a first and a second compartments separated by a flexible membrane 34 that lies in the plane of the figure. The first compartment of the pressure chamber 33 communicates with the end-cap 3 through a first portion 8a of an inlet port that extends along the central axis 9 of the end-cap 3. The first compartment of the pressure chamber 33 is also connected to the first end 4a of a pump hose 4 through a second portion 8b of the inlet port, whose longitudinal axis is perpendicular to the longitudinal axis 9 of the support 30. The first compartment of the pressure measurement chamber 33 can also be connected to a source of liquid (e.g. an infusion liquid) through a port 6 opposite to the second portion 8b of the inlet port. The second compartment of the pressure measurement chamber 33 comprises an aperture 10 for the connection to a pressure sensor for the measurement of the pressure of the liquid downstream of the pump hose 4.

The second part 32 of the pump hose support 30 also comprises a pressure measurement chamber 37 having a first and a second compartments separated by a flexible membrane 38 that lies in the plane of the figure. The first compartment of the pressure chamber 37 is connected to a supply tube 7 through a channel 39 that extends along the longitudinal axis of the pump hose support 30. The first compartment of the pressure measurement chamber 37 is also connected to the second end 4b of the pump hose 4 through a channel 40, whose longitudinal axis is perpendicular to the longitudinal axis of the support 30. The first compartment can be connected to a source of liquid by a port 6 opposite to the channel 39. The second compartment of the pressure measurement chamber 37 comprises an aperture 10 for the connection to a pressure sensor for the measurement of the pressure of the liquid upstream of the pump hose 4.

The various embodiments of the invention described above are only to exemplify the invention. The scope of the invention is therefore not limited to any of them.

The invention claimed is:

1. An end-cap assembly for closing one end of a housing of a filter, comprising:
   an end-cap having an end wall;
   an inlet port extending through the end wall for connection to a first end of a pump hose of a peristaltic pump; and
   a first holder having a first end connected to a second end of the pump hose and a second end connected to a tube,
   wherein the inlet port and the first holder are arranged relative to each other so that the pump hose forms a loop when the first end of the pump hose is connected to the inlet port and the second end of the pump hose is secured by the first end of the first holder, wherein the second end of the pump hose is configured to receive fluid from only an environment external the housing, and only the first end of the pump hose is in fluid communication with the filter.

2. An end-cap assembly according to claim 1, wherein the inlet port and the first holder are arranged relative to each other so that the loop formed by the pump hose substantially extends in a plane that is inclined with respect to a plane perpendicular to a central axis of the end-cap.

3. An end-cap assembly according to claim 1, wherein the inlet port and the first holder are arranged relative to each other so that the first end of the pump hose and the second end of the pump hose are longitudinally spaced apart from each other with respect to a central axis of the end-cap when the first end of the pump hose is connected to the inlet port and the second end of the pump hose is secured to the first end of the first holder.

4. An end-cap assembly according to claim 3, wherein the inlet port and the first holder are arranged relative to each other so that the second end of the pump hose is further apart from the end-cap than the first end of the pump hose when the first end of the pump hose is connected to the inlet port and the second end of the pump hose is secured to the first end of the first holder.

5. An end-cap assembly according to claim 1, wherein the inlet port and the first holder are arranged relative to each other so that the first end and the second end of the pump hose are adjacent to a central axis of the end-cap when the first end of the pump hose is connected to the inlet port and the second end of the pump hose is secured to the first end of the first holder.

6. An end-cap assembly according to claim 1, wherein the inlet port and the first holder are arranged relative to each other so that the first end and the second end of the pump hose are radially spaced apart from each other with respect to a central axis of the end-cap when the first end of the pump hose is connected to the inlet port and the second end of the pump hose is secured by the first holder.

7. An end-cap assembly according to claim 1, wherein the inlet port is offset with respect to a central axis of the end-cap.

8. An end-cap assembly according to claim 1, wherein the inlet port comprises a first portion furthest to the end wall, a second portion closest to the end wall, and an intermediate portion connecting the first portion to the second portion, wherein the first portion has an axis slightly inclined with respect to a plane perpendicular to a central axis of the end-cap, the second portion flares towards an interior of the end-cap along an axis generally parallel to the central axis of the end-cap, and the intermediate portion has a curvature adapted to facilitate a smooth and unimpeded flow of a liquid pumped into the end cap.

9. An end-cap assembly according to claim 1, wherein the first holder comprises a tubular connector for connecting the pump hose to a tube.

10. An end-cap assembly according to claim 1, wherein the first holder comprises a clip for snugly engaging a tubular connector for connecting the pump hose to a tube.

11. An end-cap assembly according to claim 10, wherein the tubular connector is removable and the clip is designed to resiliently engage and lock the tubular connector.

12. An end-cap assembly according to claim 1, wherein the first holder comprises a leg protruding at a periphery of the end wall of the end-cap for holding the second end of the pump hose longitudinally and radially spaced apart from a central axis of the end-cap.

13. An end-cap assembly according to claim 1, further comprising:
a second holder for holding the pump hose between the inlet port and the first holder.

14. An end-cap assembly according to claim 13, wherein the second holder comprises an arm protruding at a periphery of the end wall of the end-cap for holding the pump hose radially spaced apart from a central axis of the end-cap.

15. An end-cap assembly according to claim 1, wherein the inlet port and the first holder are arranged relative to each other so that the loop formed by the pump hose substantially extends in a plane parallel to a central axis of the end-cap when the first end of the pump hose is connected to the inlet port and the second end of the pump hose is secured by the first holder.

16. An end-cap assembly according to claim 1, wherein the first holder is removably mounted on the end-cap.

17. An end-cap assembly according to claim 1, further comprising:
at least one infusion port connected to the inlet port.

18. An end-cap assembly according to claim 1, further comprising:
a pressure measurement port connected to the inlet port for measuring a pressure of a liquid in the first end of the pump hose.

19. An end-cap assembly according to claim 1, further comprising:
at least one infusion port connected to the first holder.

20. An end-cap assembly according to claim 1, further comprising:
a pressure measurement port connected to the first holder for measuring a pressure of a liquid in the second end of the pump hose.

21. An end-cap assembly according to claim 1, wherein the pump hose has the first end fitted with a first connecting element for connection to the inlet port and the second end fitted with a second connecting element for connecting to the first holder.

22. An end-cap assembly according to claim 1, wherein the filter comprises a semi-permeable membrane for hemodialysis or hemofiltration.

23. An end-cap assembly for closing one end of a housing of a filter, comprising:
an end-cap having an end wall;
an inlet port extending through the end wall for connection to a first end of a pump hose of a peristaltic pump; and
a first holder having a first end connected to a second end of the pump hose and a second end connected to a tube,
wherein the inlet port and the first holder are arranged relative to each other so that when the first end of the pump hose is connected to the inlet port and the second end of the pump hose is secured to the first end of the first holder, the pump hose forms a loop that substantially extends in a plane parallel to a central axis of the end-cap,
wherein the second end of the pump hose is configured to receive fluid from only an environment external the housing, and only the first end of the pump hose is in fluid communication with the filter.

24. An end-cap assembly for closing one end of a housing of a filter, comprising:
an end-cap having an end wall;
an inlet port extending through the end wall for connection to a first end of a pump hose of a peristaltic pump; and
a first holder having a first end connected to a second end of the pump hose and a second end connected to a tube, wherein the inlet port and the first holder are arranged relative to each other so that when the first end of the pump hose is connected to the inlet port and the second end of the pump hose is secured to the first end of the first holder, the pump hose forms a loop and the first end of the pump hose and the second end of the pump hose are longitudinally spaced apart from each other with respect to a central axis of the end-cap, wherein the second end of the pump hose is configured to receive fluid from only an environment external the housing, and only the first end of the pump hose is in fluid communication with the filter.

25. An end-cap assembly for closing one end of a housing of a filter, comprising:

an end-cap having an end wall;

an inlet port extending through the end wall for connection to a first end of a pump hose of a peristaltic pump; and a first holder having a first end connected to a second end of the pump hose and a second end connected to a tube, wherein the inlet port and the first holder are arranged relative to each other so that when the first end of the pump hose is connected to the inlet port and the second end of the pump hose is secured to the first end of the first holder, the pump hose forms a loop and the first end of the pump hose and the second end of the pump hose are adjacent to a central axis of the end-cap, wherein the second end of the pump hose is configured to receive fluid from only an environment external the housing, and only the first end of the pump hose is in fluid communication with the filter.

* * * * *